United States Patent
Wollowitz et al.

(10) Patent No.: US 12,409,258 B2
(45) Date of Patent: Sep. 9, 2025

(54) PRESSURE SENSORS, INCLUDING PRESSURE SENSORS FOR AUTOMATED PERITONEAL DIALYSIS SYSTEMS, AND ASSOCIATED SYSTEMS, DEVICES, AND METHODS

(71) Applicant: Byonyks Medical Devices, Inc., Itasca, IL (US)

(72) Inventors: Michael Wollowitz, Chatham, NY (US); Abdul Qadeer, Lahore (PK); Farrukh Usman, Chatham, NY (US)

(73) Assignee: Byonyks Medical Devices, Inc., Itasca, IL (US)

( * ) Notice: Subject to any disclaimer, the term of this patent is extended or adjusted under 35 U.S.C. 154(b) by 467 days.

(21) Appl. No.: 18/017,619

(22) PCT Filed: Jul. 27, 2021

(86) PCT No.: PCT/US2021/071012
§ 371 (c)(1),
(2) Date: Jan. 23, 2023

(87) PCT Pub. No.: WO2022/027036
PCT Pub. Date: Feb. 3, 2022

(65) Prior Publication Data
US 2023/0293796 A1 Sep. 21, 2023

Related U.S. Application Data

(60) Provisional application No. 63/056,879, filed on Jul. 27, 2020.

(51) Int. Cl.
*A61M 1/28* (2006.01)
*A61M 1/14* (2006.01)
(Continued)

(52) U.S. Cl.
CPC .......... *A61M 1/282* (2014.02); *A61M 1/1524* (2022.05); *A61M 1/154* (2022.05);
(Continued)

(58) Field of Classification Search
CPC .... A61M 1/1524; A61M 1/154; A61M 1/159; A61M 1/16; A61M 1/28; A61M 1/282;
(Continued)

(56) References Cited

U.S. PATENT DOCUMENTS

2002/0073782 A1 6/2002 Chevallet et al.
2002/0120227 A1 8/2002 Childers et al.
(Continued)

FOREIGN PATENT DOCUMENTS

WO 2021211803 A1 10/2021
WO 2022040325 A2 2/2022
(Continued)

OTHER PUBLICATIONS

International Search Report and Written Opinion dated Oct. 21, 2021 issued in International Patent Application No. PCT/US2021/071012.
(Continued)

*Primary Examiner* — John Kim
(74) *Attorney, Agent, or Firm* — McDonnell Boehnen Hulbert & Berghoff LLP

(57) ABSTRACT

Pressure sensors, including pressure sensors for automated peritoneal dialysis (APD) systems, and associated systems, devices, and methods are disclosed herein. In one embodiment, an APD system includes a diaphragm positioned over an opening in a disposable set that includes one or more fluid lines. The diaphragm is affixed to the disposable set about a periphery of the opening. The APD system further includes a pressure sensor configured to measure a pressure of fluid flowing through the disposable set. The pressure sensor
(Continued)

includes a load cell and an indenter. The indenter can be moveable along an axis such that, when the diaphragm is aligned with the axis, a convexly curved surface of the indenter can be positioned against the diaphragm. When the indenter is contacting the diaphragm, the load cell can measure a force applied to the load cell by the diaphragm and/or by the fluid flowing through the disposable set.

20 Claims, 6 Drawing Sheets

(51) Int. Cl.
  *A61M 1/16* (2006.01)
  *A61M 1/36* (2006.01)
  *F16K 7/12* (2006.01)
  *G01L 7/08* (2006.01)
  *G01L 9/00* (2006.01)
(52) U.S. Cl.
  CPC .............. *A61M 1/159* (2022.05); *A61M 1/16* (2013.01); *A61M 1/28* (2013.01); *A61M 1/36* (2013.01); *A61M 1/3639* (2013.01); *F16K 7/12* (2013.01); *G01L 7/08* (2013.01); *G01L 9/0041* (2013.01); *A61M 2205/273* (2013.01); *A61M 2205/332* (2013.01); *A61M 2205/3327* (2013.01); *A61M 2205/3331* (2013.01); *A61M 2205/3344* (2013.01)

(58) Field of Classification Search
  CPC .............. A61M 1/36; A61M 1/3639; A61M 2205/273; A61M 2205/332; A61M 2205/3327; A61M 2205/3331; A61M 2205/3344; F16K 7/12; G01L 7/08; G01L 9/0041
  See application file for complete search history.

(56) References Cited

U.S. PATENT DOCUMENTS

| 2003/0200812 | A1 | 10/2003 | Kuhn et al. |
| 2006/0278001 | A1 | 12/2006 | Kaneko et al. |
| 2012/0267291 | A1 | 10/2012 | Coates |
| 2014/0018727 | A1 | 1/2014 | Burbank et al. |
| 2014/0076058 | A1 | 3/2014 | Brugger et al. |
| 2019/0275228 | A1 | 9/2019 | Crawford et al. |

FOREIGN PATENT DOCUMENTS

| WO | 2022040597 A1 | 2/2022 |
| WO | 2022040601 A1 | 2/2022 |
| WO | 2022051456 A1 | 3/2022 |
| WO | 2022/236053 A | 11/2022 |

OTHER PUBLICATIONS

Extended European Search Report issued Jun. 19, 2024, in corresponding European Application No. 21849916.8, 7 pages.

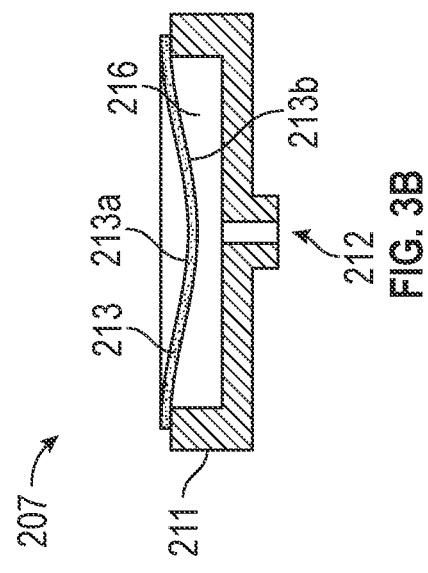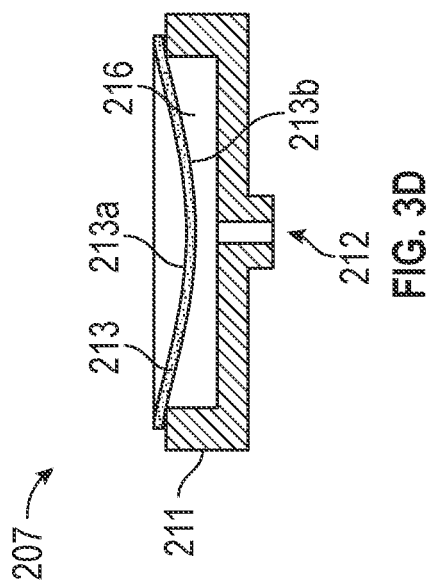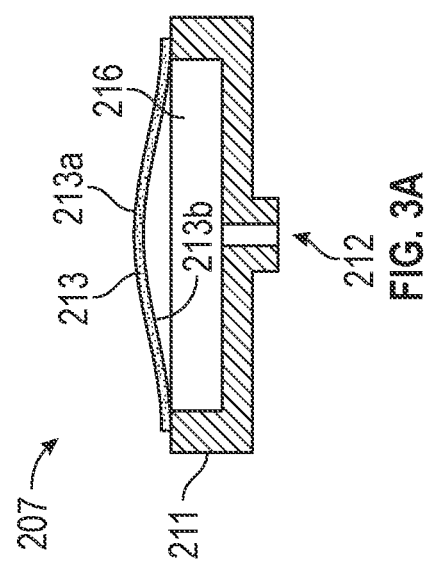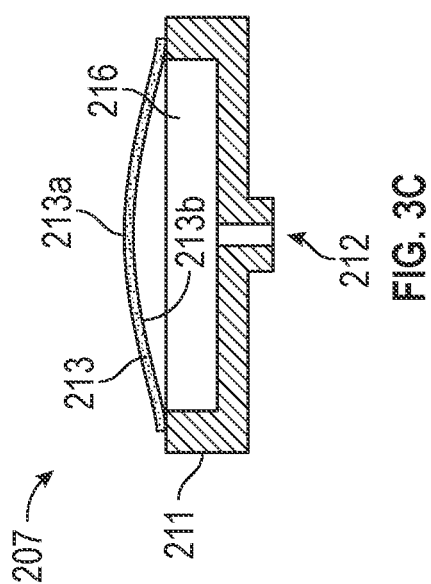

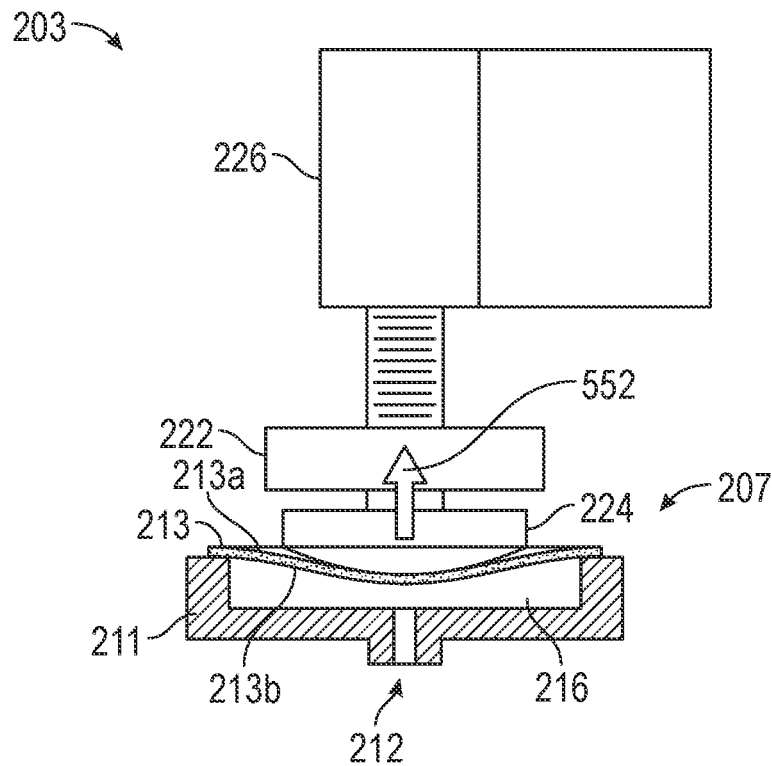
FIG. 5A
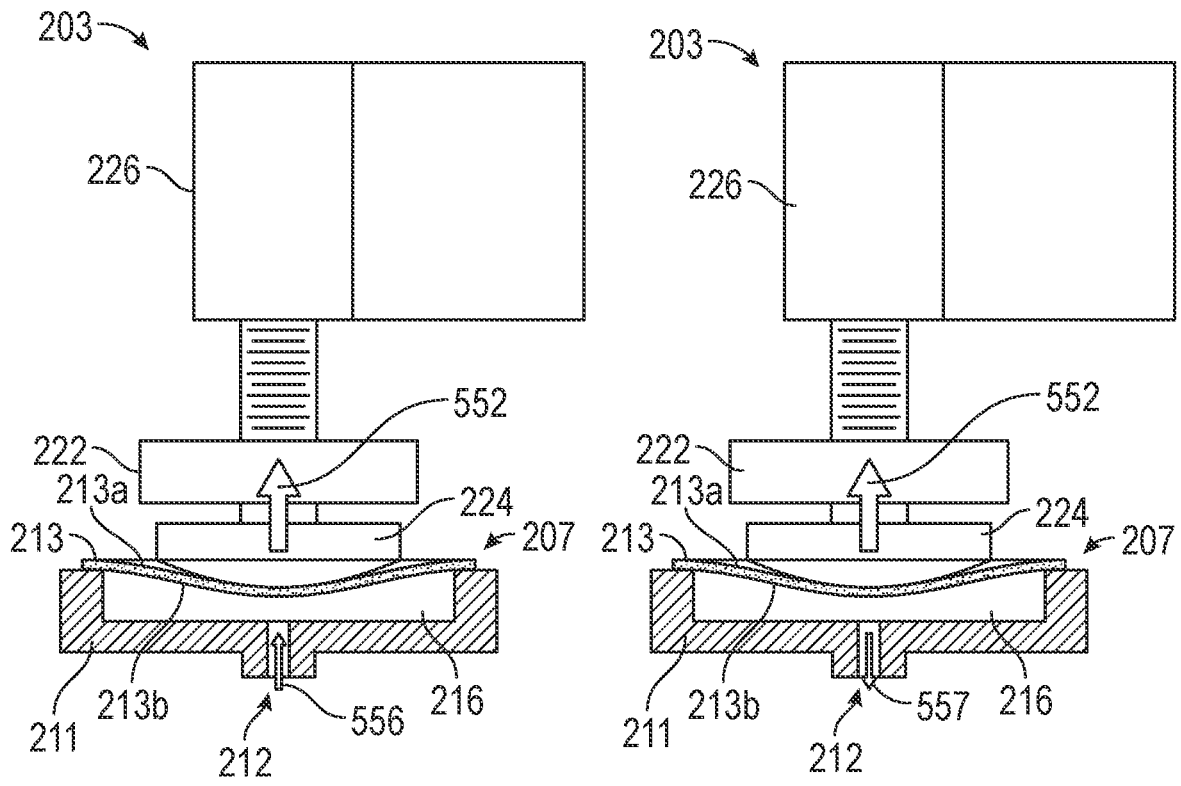
FIG. 5B
FIG. 5C

PRESSURE SENSORS, INCLUDING PRESSURE SENSORS FOR AUTOMATED PERITONEAL DIALYSIS SYSTEMS, AND ASSOCIATED SYSTEMS, DEVICES, AND METHODS

CROSS-REFERENCE TO RELATED APPLICATION(S)

This application is a 371 U.S. national phase of PCT/US2021/071012, filed Jul. 27, 2021, which claims the benefit of priority from U.S. Provisional Patent Application No. 63/056,879, filed Jul. 27, 2020, both of which are incorporated by reference herein in their entirety.

TECHNICAL FIELD

The present disclosure is directed to pressure sensors, including pressure sensors for automated peritoneal dialysis (APD) systems, and associated systems, devices, and methods. For example, pressure sensors configured in accordance with some embodiments of the present technology are configured to measure pressure of isolated solutions flowing through disposable sets of APD systems.

BACKGROUND

Dialysis is used to (a) remove excess fluid and toxins in persons with kidney failure and (b) correct electrolyte concentrations in their blood. Peritoneal dialysis is a form of dialysis that uses a peritoneum in an individual's abdomen as a membrane through which fluid and dissolved substances are exchanged with blood. More specifically, a solution is introduced into and removed from the individual's abdomen via a surgically installed catheter.

In continuous ambulatory dialysis (CAPD), solution is manually introduced and removed (e.g., at regular intervals throughout the day). In particular, the catheter is connected to a disposable set (also known as a transfer set) that includes (i) a source bag (e.g., hung on a drip stand) containing new solution, (ii) a drain bag configured to collect waste solution, and (iii) various fluid lines connecting the source bag and the drain bag to the catheter. Waste solution from the individual's lower abdomen is drained into the drain bag via the catheter, and new solution is introduced into the individual's lower abdomen via the catheter. After such an exchange treatment is complete, the disposable set is discarded.

APD (also known as continuous cycling peritoneal dialysis (CCPD)) is similar to CAPD except that the exchange treatment is automated using an APD machine or cycler. More specifically, a pump included in the APD machine is used to introduce and remove the solution (e.g., while the individual sleeps). Each APD exchange treatment may include one or more cycles of introducing and removing solution from the individual's abdomen.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. The drawings should not be taken to limit the disclosure to the specific embodiments depicted, but are for explanation and understanding only.

FIGS. 3A-3D are partially schematic, cross-sectional, side views of a portion of a disposable set configured in accordance with various embodiments of the present technology.

FIGS. 5A-5C are partially schematic, side views of a pressure sensor and a partially schematic, cross-sectional, side view of a portion of a disposable set, each configured in accordance with various embodiments of the present technology.

DETAILED DESCRIPTION

Figure 1:
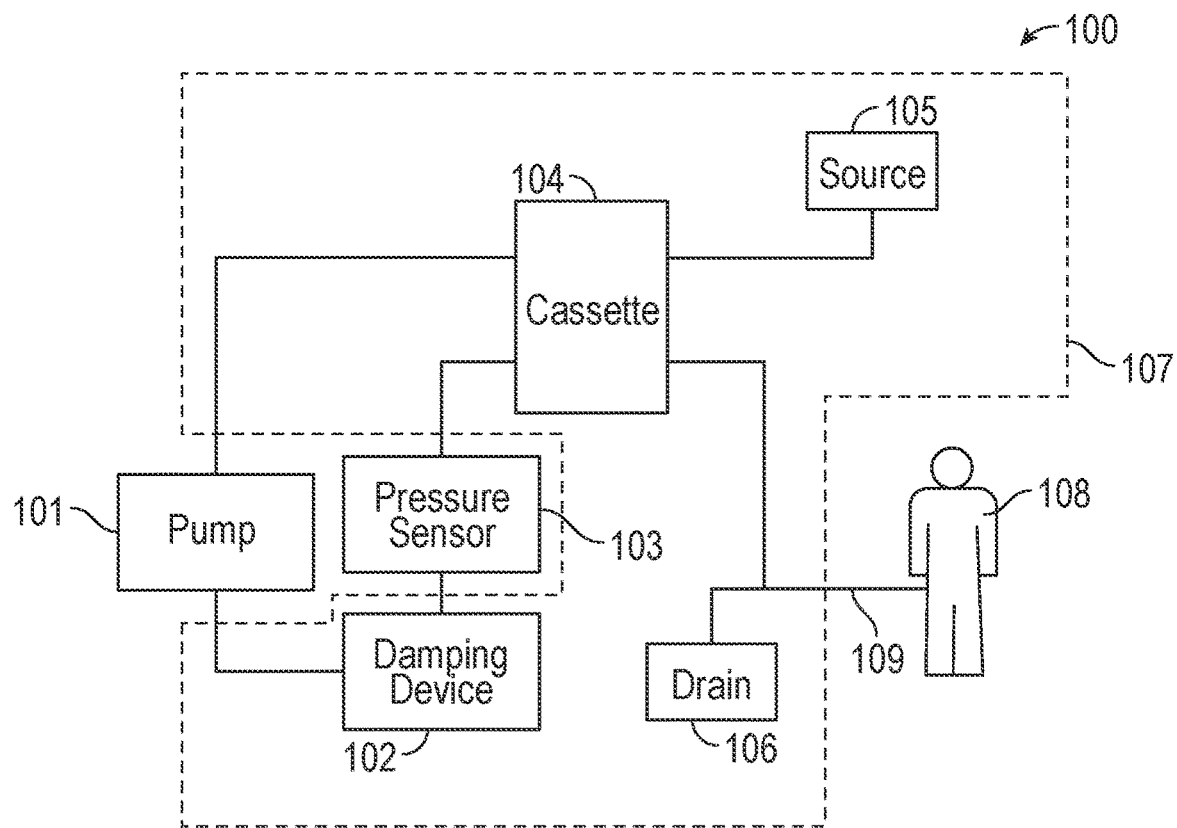
FIG. 1 is a partially schematic representation of an automated peritoneal dialysis system configured in accordance with various embodiments of the present technology.

The present disclosure is directed to pressure sensors and associated systems, devices, and methods. In the illustrated embodiments below, pressure sensors of the present technology are primarily described in the context of measuring pressure of dialysate solution flowing through disposable sets of APD systems. Pressure sensors configured in accordance with various embodiments of the present technology, however, can be incorporated into and/or used by other systems, including hemodialysis systems and/or other medical or non-medical systems. Additionally, pressure sensors of the present technology can be used measure pressure of solutions or fluids besides dialysate solution, such as water, saline, blood, and/or other low viscous fluids. Furthermore, a person skilled in the art will understand (i) that the technology may have additional embodiments than illustrated in FIGS. 1-8 and (ii) that the technology may be practiced without several of the details of the embodiments described below with reference to FIGS. 1-8.

A. OVERVIEW

Many systems include pumps (e.g., non-invasive pumps, peristaltic pumps, etc.) configured to regulate, control, and/or otherwise affect fluid flow through other components of the systems. For example, pumps are commonly used to perform blood transfusions and cardiopulmonary bypass operations. Pumps are also used in many industrial applications, such as in agriculture or in food dispensing. The act of pumping fluid creates fluid pressures within a system that can vary as the system is operated. In some systems, fluid pressures must remain within predetermined operating ranges to ensure safe or proper operation of the systems. For example, in some medical systems, when fluid pressure exceeds or violates safe operating limits, a patient may experience harm or discomfort. Thus, pressure sensors can be employed to monitor fluid pressure and ensure that the fluid pressures remain within safe operating ranges.

For certain systems (e.g., medical systems, laboratory systems, food dispensing systems, etc.), measuring and monitoring fluid pressure can be difficult because a fluid flowing through the systems must remain isolated to prevent contamination. In some of these systems, a disposable set of fluid lines and/or other components is used to convey fluid from a sterile container to a destination (e.g., a patient, a storage container, etc.). The disposable set can be pre-sterilized and disposed of after a single use to minimize the risk of contamination.

To measure fluid pressure in a disposable set, many systems use a pressure transducer that operates by converting (a) pressure of a fluid against a surface in contact with the fluid into (b) a displacement of some mechanical element (e.g., a force sensor) of the pressure transducer. Commonly, the displacement is then converted into an electrical signal that can be used to monitor the fluid pressure. For example, some industrial systems thread or press a pressure transducer into a port on a container or pipe. Such a solution has two primary drawbacks: (1) any port that opens into a sterile containment system is a potential source of contamination, and (2) the pressure transducer itself must be sterilized between uses and remains a potential source of contamination.

Another approach includes placing a thin, flexible membrane over an opening into a fluid containment system. The membrane has excess material so that it can deform with little resistance. A pressure transducer is centered on the membrane, and internal fluid pressure forces the membrane against a surface of the pressure transducer. A measured force can be used to approximate the internal pressure of fluid.

The above approach has previously been employed in hemodialysis systems. In a hemodialysis system, however, blood pressure ranges from about +6 kPa to about +30 kPa. Thus, the above approach is typically only used to measure positive fluid pressures. In addition, the membrane used in such a system is often fragile (e.g., easily deformed, extremely flexible, not rigid, not semi-rigid, etc.). Furthermore, the surface of the pressure transducer in contact with membrane is typically (a) planar and (b) much smaller than the opening in the disposable set transporting blood. When the planar surface contacts and/or deforms the membrane, the membrane is often stretched (e.g., at edges of the planar surface) and/or is not uniformly or smoothly deformed. This can lead to inaccuracies in pressure measurements captured by the pressure transducer and/or to inelastic deformation of the membrane. Furthermore, the planar surface does not fully support the membrane when the membrane is deformed, and the size of the planar surface (being much smaller than the opening) requires precise positioning of the surface at the center of the membrane for accurate measurement of blood pressure. As a result, such pressure transducers are often sensitive to variations in (i) thicknesses or moduli between different membranes of different disposable sets and/or (ii) different placements of the planar surface is relation to the center of the membrane. Therefore, complex analysis and experimentation is often required for each membrane and/or positioning of the planar surface to determine a relationship between a force measured by the pressure transducer and pressure of blood within the hemodialysis system.

Another approach that is used in applications in which high accuracy and measurement of low pressures are not needed involves measuring pressure in a soft elastomeric tube containing a pressurized fluid. The tube is partially flattened between two plates that are pressed against the tube from opposite sides. One of the plates is mounted on a force sensor. When fluid pressure within the tube works to restore a circular cross-section of the tube, the fluid pressure presses the tube against the plates and registers a force on the force sensor. The force can be used to approximate the pressure of the fluid within the tube.

In this approach, however, it is difficult (a) to maintain a consistent deformation of the tube and/or (b) to ensure that a force applied to restore the circular cross-section of the tube is fully transmitted to the force sensor. In addition, a large portion of a force measured by the force sensor is often due to a force provided by the tube itself to restore its circular cross-section rather than due to pressure of the fluid. Furthermore, this approach is often highly sensitive to variations in wall thickness, hardness, and/or other properties between different tubes. Moreover, it is difficult to measure negative pressures using this approach.

Apart from pressure transducers, another approach used to measure fluid pressure in a disposable set involves including an electronic pressure sensor in the disposable set. In this approach, electrical leads of the sensor extend from an interior of the disposable set to contacts on an exterior of the disposable set. The disposable set (including the electronic pressure sensor) is sterilized before use and is then thrown away after use to eliminate the risk of contamination. Such an approach is therefore expensive and wasteful as the electronic pressure sensor is used only once.

One other approach is commonly used in APD systems in which dialysate is pumped into and out of a patient's body. More specifically. APD systems typically employ systems that control fluid pressure by measuring air pressure external to the isolated, sterile dialysate. Such systems are often extremely expensive and complex.

To address the shortcomings of the approaches described above, the inventors have developed pressure systems and associated systems, devices, and methods that are expected to safely, accurately, and affordably measure pressure of an isolated fluid (e.g., flowing within a disposable set). In one embodiment, a diaphragm is positioned over an opening in a disposable set that includes one or more fluid lines. The diaphragm is affixed to the disposable set about a periphery of the opening. The APD system further includes a pressure sensor configured to measure a pressure of fluid flowing through the disposable set. The pressure sensor can include a load cell and an indenter. The indenter can be moveable along an axis such that, when the diaphragm is aligned with the axis, a convex, arced, or curved surface of the indenter can be positioned against and deform the diaphragm. When the indenter is contacting the diaphragm, the load cell can measure a force applied to the load cell by the diaphragm and/or by the fluid flowing through the disposable set. The force can be used to determine a pressure of the fluid flowing through the disposable set. In this manner, pressure sensors of the present technology can be used to monitor fluid pressures flowing through a disposable set and/or to increase the likelihood that the fluid pressures remain within safe operating ranges.

Pressure sensors and associated systems, devices, and methods of the present technology therefore offer several advantages. For example, the pressure sensor of the present technology indirectly contacts fluid via a diaphragm of a disposable set. Thus, the fluid can remain isolated within the disposable set (thereby reducing the risk of contaminating the fluid), and the pressure sensor can be repeatedly reused to measure pressure of fluid flowing through a plurality of different disposable sets (thereby reducing waste and costs of the system). Furthermore, the indenter can include a shaped (e.g., convex, curved, arced, non-planar) surface that contacts the diaphragm. For example, the surface can generally match a curvature of the diaphragm due to fluid pressure alone. Thus, the indenter can uniformly and/or smoothly deform the diaphragm with little to no stretching or inelastic deformation. In addition, the shaped surface helps facilitate transferring most or all of the force applied against the diaphragm due to pressure of fluid flowing through a disposable set to the load cell via the indenter, thereby increasing the accuracy of pressure measurements of the fluid.

Moreover, the indenter can be sized such that (a) a contact area between the indenter and the diaphragm is approximately equivalent to a surface area of the diaphragm and (b) the diaphragm is fully supported while being deformed by the indenter. As a result, a calculation of fluid pressure from a force measured by the load cell of the pressure sensor is simplified and/or requires little to no analysis or experimentation to determine a relationship between the measured force and the pressure of the fluid. In addition, the present technology is less sensitive to variations in thickness, hardness, and/or other properties between diaphragms, meaning that the present technology can repeatedly provide accurate pressure measurements across different disposable sets.

Further, the present technology can factor out (a) a zero-offset force corresponding to a restoring force of the diaphragm alone when the diaphragm is deformed by the indenter from (b) a force measured by the load cell of the pressure sensor. Thus, pressure sensors of the present technology can accurately determine a force acting upon the indenter through the diaphragm by pressure of the fluid alone. Additionally, pressure sensors of the present technology can measure both positive and negative pressures in fluid flowing through a disposable set. As such, the present technology is particularly apt for APD and other systems that involve both infusion and aspiration of fluid. For example, the present technology can measure both a range of positive fluid pressures (e.g., 0 kPa to +10 kPa) that is commonly observed when introducing dialysate into a patient during a cycle of an APD treatment and a range of negative fluid pressures (e.g., 0 kPa to −10 kPa) that is commonly observed when removing dialysate from a patient during a cycle of an APD treatment.

B. SELECTED EMBODIMENTS OF PRESSURE SENSORS, INCLUDING PRESSURE SENSORS FOR APD SYSTEMS, AND ASSOCIATED SYSTEMS, DEVICES AND METHODS

FIG. 1 is a partially schematic representation of an APD system 100 ("the system 100") configured in accordance with various embodiments of the present technology. As shown, the system 100 includes a pump 101, a pressure sensor 103, and a disposable set 107. The disposable set 107 of FIG. 1 includes a damping device 102, a cassette 104, a source bag 105, a drain bag 106, and various fluid lines extending between components of the disposable set 107, the pressure sensor 103, and/or the pump 101. Other well-known components of APD systems are not illustrated in FIG. 1 or described in detail below so as to avoid unnecessarily obscuring aspects of the present technology.

In some embodiments, the pump 101 can be a non-invasive pump. For example, the pump 101 can be a peristaltic pump or another suitable type of pump. In these and other embodiments, the pump 101 and/or the pressure sensor 103 can be removably or permanently integrated into an APD machine or cycler (not shown). Alternatively, the pump 101 and/or the pressure sensor 103 can be components of the system 100 that are separate from an APD machine or cycler.

Various components of the disposable set 107 can interface with an APD machine. For example, the damping device 102 can be installed on (e.g., held in place, attached to, supported by, etc.) an APD machine during an exchange treatment. As another example, a portion of the disposable set that includes a diaphragm or membrane (not shown) can be mounted or otherwise positioned on an APD machine and/or aligned with the pressure sensor 103, as discussed in greater detail below. The disposable set 107 can be configured to interface (a) with the pump 101, (b) with the pressure sensor 103, and (c) with a catheter 109 installed in a patient 108. For example, the disposable set 107 can connect to the catheter 109 such that the catheter 109 is placed in fluid communication with the source bag 105 and/or the drain bag 106.

In operation, the system 100 can be configured to introduce solution (e.g., dialysate or another fluid initially contained within the source bag 105) into the patient 108 using the pump 101 and/or via at least a first portion of the disposable set 107. The system 100 can further be configured to remove solution from the patient 108 by draining the solution into the drain bag 106 using the pump 101 and/or via at least a second portion of the disposable set 107. In some embodiments, a single exchange treatment can include one or more cycles of introducing solution into the patient 108 and removing solution from the patient 108. After an exchange treatment is complete, the disposable set 107 can be discarded and a separate (e.g., a new) disposable set 107 can be used for a subsequent treatment.

The damping device 102 of the disposable set 107 can be configured to control, reduce, and/or minimize amplitudes of pressure pulsations in solution flowing through the damping device 102 and/or other components of the disposable set 107. For example, the damping device 102 can reduce amplitudes of positive and/or negative pressure pulsations that are induced in the solution by the pump 101 such that solution flow through the disposable set 107 is smoothed. This is expected to reduce, minimize, and/or eliminate patient discomfort while solution is pumped into and/or out of the patient 108. In these and other embodiments, the damping device 102 can be configured to remove air bubbles from solution within the damping device 102, which is expected to further reduce, minimize, and/or eliminate the possibility of patient discomfort or harm during an exchange treatment.

The pressure sensor 103 can be configured to measure pressure of solution flowing through at least a portion of the disposable set 107. For example, as discussed in greater detail below, the pressure sensor 103 can (a) be aligned with a portion of the disposable set 107 and (b) be configured to measure pressure of solution flowing through the portion of the disposable set 107 without the pressure sensor 103 coming in contact with the solution. The portion of the disposable set 107 aligned with the pressure sensor 103 can include a portion (e.g., a diaphragm or membrane) of the damping device 102, or the portion of the disposable set 107 aligned with the pressure sensor 103 can be separate from the damping device 102. As discussed in greater detail below, the system 100 can monitor pressure measurements captured by the pressure sensor 103 and compare the pressure measurements to one or more safe operating thresholds or ranges. In these and other embodiments, the system 100 can interrupt an exchange treatment or cycle when one or more pressure measurements violate (e.g., exceed and/or drop below) the one or more safe operating thresholds or ranges.

Figure 2:
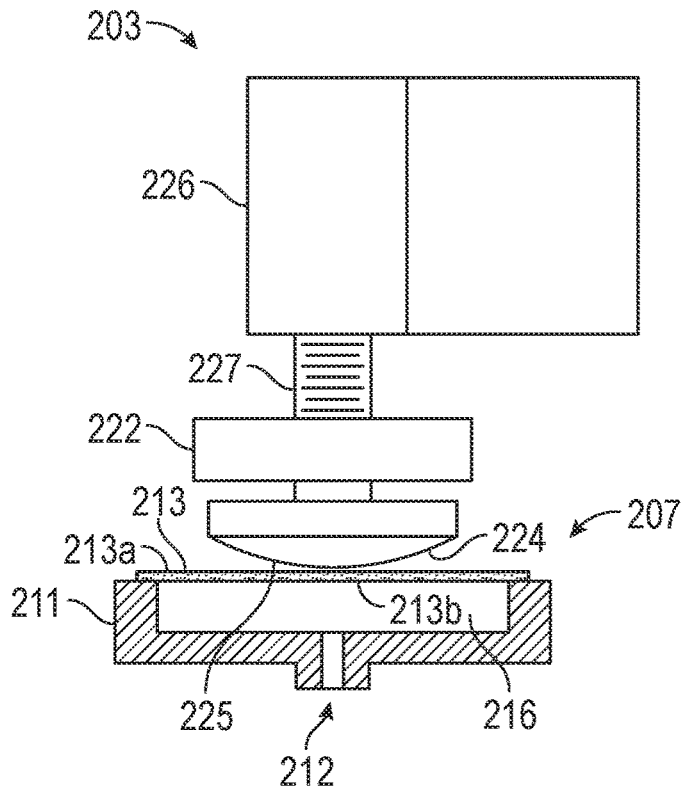
FIG. 2 is a partially schematic, side view of a pressure sensor and a partially schematic, cross-sectional, side view of a portion of a disposable set, each configured in accordance with various embodiments of the present technology.

FIG. 2 is a partially schematic, side view of a pressure sensor 203 and a partially schematic, cross-sectional, side view of a portion 207 of a disposable set, each configured in accordance with various embodiments of the present technology. The pressure sensor 203 can be the pressure sensor 103 of FIG. 1 or another pressure sensor of the present technology. Additionally, or alternatively, the portion 207 can be a portion of the disposable set 107 of FIG. 1 or another disposable set configured in accordance with the present technology.

Referring first to the pressure sensor 203, the pressure sensor 203 includes an indenter 224, a linear actuator 226, and a load cell 222 positioned between the indenter 224 and the linear actuator 226. The load cell 222 (also known as a force sensor) has a generally cylindrical or disk shape in FIG. 2, but the load cell 222 can have a different shape in other embodiments. For example, the load cell 222 can have a generally block or rectangular shape.

As discussed in greater detail below, the load cell 222 is configured to produce an electrical signal in response to a force applied against the load cell 222 (e.g., in response to a force applied to the indenter 224 generally parallel and/or along an axis passing through the indenter 224, the load cell 222, and the linear actuator 226 in FIG. 2). In some embodiments, the load cell 222 can be operable to measure compressive forces (e.g., forces that push the indenter 224 toward the load cell 222). For example, for measuring pressure of solution flowing through a disposable set of an APD system, the load cell 222 can be configured to measure a range of forces corresponding to a pressure range of about 0 kPa to about 50 kPa (e.g., about 5 kPa to about 45 kPa). Additionally, or alternatively, the load cell 222 can be operable to measure tensive forces (e.g., forces that pull the indenter 224 away from the load cell 222).

In the illustrated embodiment, the load cell 222 is affixed to the indenter 224. In particular, the indenter 224 is affixed to and/or centered on a force contact area of the load cell 222 such that force applied to the indenter 224 is transmitted to and/or is measurable by the load cell 222. In some embodiments, an outer surface 225 of the indenter 224 is shaped (i.e., not planar). For example, as shown in FIG. 2, the outer contacting surface 225 of the indenter 224 can be (e.g., smoothly) convex, arced, or curved. As discussed in greater detail below, the curved shaped of the indenter 224 can facilitate positioning the indenter 224 against an outer surface 213a of a diaphragm 213 (e.g., a membrane, an elastic portion, etc.) of the portion 207 of the disposable set and deforming the diaphragm 213 (a) such that the outer surface 225 of the indenter 224 matches a natural curvature of the diaphragm 213 due to fluid pressure alone and/or (b) such that a contact area between the outer surface 225 of the indenter 224 and the diaphragm 213 is nearly equivalent to a total surface area of either the outer surface 213a or an inner surface 213b of the diaphragm 213. Such an arrangement between the outer surface 225 of the indenter 224 and the diaphragm 213 can facilitate transmitting nearly all of a force applied against an inner surface 213b of the diaphragm 213 to the load cell 222 and can greatly simplify calculation of pressure from force measurements captured by the load cell 222. Nevertheless, the outer surface 225 of the indenter 224 can include a different shape in other embodiments of the present technology, such as a planar or triangular shape.

The load cell 222 can be further affixed to the linear actuator 226. For example, a body of the load cell 222 can be affixed to a linearly movable component 227 of the linear actuator 226. In the illustrated embodiment, the linear actuator 226 is a lead screw mechanism that is configured to translate or move the load cell 222 and the indenter 224 generally along an axis extending through the indenter 224, the load cell 222, and the linear actuator 226. For example, the linear actuator 226 can translate the load cell 222 and the indenter 224 in fine increments over a given range (e.g., 1 mm to 10 mm). In some embodiments, the linear actuator 226 can include a small mechanical tolerance to facilitate precisely retaining and/or precisely, repeatedly positioning the indenter 224 at a location. In these and other embodiments, the linear actuator 226 can constrain movement of the load cell 222 and the indenter 224 to only along the axis along which the linear actuator 226 is configured to translate the load cell 222 and the indenter 224.

In some embodiments, the linear actuator 226 can be manually operated. In other embodiments, however, the linear actuator 226 can be driven by a motor (not shown), such as by an electric motor with or without additional gear reduction. Other methods of linear actuation and/or linear guidance can be employed and are within the scope of the present technology. For example, a linear sliding cam or wedge, a pneumatic or hydraulic actuator of cylinder or bellows type, a piezo-electric actuator, and/or a four-bar linkage can be employed in addition to or in lieu of an electric motor.

In some embodiments, a microcontroller (not shown) can be used to control the linear actuator 226 to (e.g., automatically) translate the load cell 222 and the indenter 224. Additionally, or alternatively, the microcontroller can monitor force measurements captured by the load cell 222 and/or can use the captured force measurements as feedback for positioning of the load cell 222 and the shaped indenter 224. For example, as described in greater detail below, the microcontroller can control the electric motor to advance the load cell 222 and the indenter 224 against the outer surface 213a of the diaphragm 213 until force measurements captured by the load cell 222 reach a desired magnitude.

As discussed above, the portion 207 of the disposable set illustrated in FIG. 2 includes a diaphragm 213 having an outer surface 213a and an inner surface 213b opposite the outer surface 213a. The portion 207 further includes a rim structure 211 and a port 212 (e.g., a tube, a channel, etc.). In some embodiments, the diaphragm 213 is affixed (e.g., hermetically and/or using an adhesive) to the rim structure 211 at a periphery of an opening at a top portion of the rim structure 211. In other embodiments, the diaphragm 213 can be integrated with the rim structure 211. For example, the diaphragm 213 and the rim structure 211 can be molded as a single component, with a portion of the single component corresponding to the diaphragm 213 being thinner and more flexible than a portion of the single component corresponding to the rim structure 211.

The rim structure 211 and/or the diaphragm define (at least in part) a cavity 216. The cavity 216 can be rigid (e.g., at least along the portions corresponding to the rim structure 211). Additionally, or alternatively, the cavity 216 can be closed (e.g., hermetically sealed) by the rim structure 211 and the diaphragm 213 except for the port 212. The port 212 can fluidly connect the cavity 216 to fluid lines (not shown) or other portions of the disposable set. In these embodiments, as fluid flows through the disposable set, the fluid can enter the cavity 216 via the port and exert a force a force on the diaphragm 213. As discussed in greater detail below, when the pressure sensor 103, when aligned with and contacting the diaphragm 213, can measure the force exerted on the indenter 224 of the pressure sensor through the diaphragm 213 to determine a pressure of the fluid within the cavity 216 and/or flowing through the disposable set. Although shown within only one port 212 in FIG. 2, the portion 207 of the disposable set can include a greater number of ports 212 (e.g., an inlet port 212 and an outlet port 212) in other embodiments of the present technology.

As shown in FIG. 2, the diaphragm 213 has a thin, sheet-like structure. The diaphragm 213 can be opaque or transparent. In some embodiments, at least the outer surface 213a of the diaphragm 213 is smooth and/or has a relatively low coefficient of friction. The material(s) used to form the diaphragm 213, the thickness of the diaphragm 213, and/or the size/shape of the diaphragm 213 can depend on a range of pressures to be applied to the diaphragm 213, a type of fluid applying the pressure, and/or the required accuracy of pressure measurements calculated from forces measured by the load cell 222. For example, the diaphragm 213 can be made of metal, ceramic, glass, and/or polymer (e.g., polycarbonate, polyethylene terephthalate (PET), polymethylpentene, etc.) depending upon application. As another particular example, the diaphragm 213 can have (a) a diameter from about 15 mm to about 40 mm and/or (b) a thickness ranging from about 0.2 mm to about 0.5 mm. In some embodiments, the size and/or shape of the diaphragm 213 can correspond to the opening in the rim structure 211 of the cavity 216. Thus, in the illustrated embodiment, the diaphragm 213 has a circular or disk shape to match a circular or disk shape of the opening in the rim structure 211. Other shapes (e.g., triangular, rectangular, pentagonal, etc.) and dimensions for the diaphragm 213 and/or the opening of the rim structure 211 are of course possible and within the scope of the present technology.

The diaphragm 213 can be a rigid, semi-rigid, or semi-flexible structure. In some embodiments, a positive internal pressure within the cavity 216 (relative to external pressure) will cause the diaphragm 213 to deform outwardly while a negative internal pressure within the cavity 216 (relative to external pressure) will cause the diaphragm 213 to deform inwardly. FIGS. 3A-3D, for example, illustrate various possible deformations of the diaphragm 213. The amount of deformation illustrated in FIGS. 3A-3D is greatly exaggerated for the sake of clarity and understanding. In actuality, the amount of deformation is often not readily perceivable.

In FIGS. 3A and 3B, the diaphragm 213 and the rim structure 211 include a clamp-type joint at locations where the diaphragm 213 is affixed to the rim structure 211. Thus, the diaphragm 213 deforms primarily by bending. More specifically, a central part of the diaphragm 213 deforms with a curvature opposite that of an outer part of the diaphragm 213. For positive pressure within the cavity 216 (FIG. 3A), the central part of the diaphragm 213 bends outwardly such that it is convex (viewed from outside the cavity 216) while the outer part of the diaphragm 213 is concave. For negative pressure within the cavity 216 (FIG. 3B), the central part of the diaphragm bends inwardly such that it is concave (viewed from outside the cavity 216) while the outer part of the diaphragm 213 is convex.

In FIGS. 3C and 3D, the diaphragm 213 and the rim structure 211 include a flexible-type joint at locations where the diaphragm 213 is affixed to the rim structure 211. Thus, the diaphragm 213 deforms primarily by stretching. More specifically, most or all of the diaphragm 213 deforms with a same curvature. For positive pressure within the cavity 216 (FIG. 3C), both the central part and the outer part of the diaphragm 213 bend outwardly such that they are convex (viewed from outside the cavity 216). For negative pressure within the cavity 216 (FIG. 3D), both the central part and the outer part of the diaphragm 213 bend inwardly such that they are concave (viewed from outside the cavity 216). This type of deformation of the diaphragm 213 often occurs when the maximum displacement (e.g., at the center) of the diaphragm 213) is somewhat greater than the thickness of the diaphragm 213.

As discussed above, fluid enters the cavity 216 of the portion 207 of the disposable set via the port 212 and exerts a force against the diaphragm 213. The force is related to a pressure of the fluid within the cavity 216. Thus, when fluid pressure is positive, the fluid exerts a force that causes the diaphragm 213 to deform outwardly. When fluid pressure is negative, the fluid exerts a force that causes the diaphragm 213 to deform inwardly. By positioning the indenter 224 of the pressure sensor 203 against the outer surface 213a of the diaphragm 213, the load cell 222 of the pressure sensor 203 can measure a force exerted on the indenter 224 by fluid through the diaphragm 213 and use the force measurement to determine a pressure of the fluid without coming into contact with the fluid. Therefore, when the fluid is dialysate or another medical solution flowing through a disposable set (e.g., for introduction into a patient), the fluid can remain isolated (thereby reducing the risk of contaminating the fluid before introduction of the fluid into the patient), and the pressure sensor 203 can calculate a pressure of the fluid flowing through the disposable set. In turn, pressure measurements captured by the pressure sensor 203 can be monitored to ensure that the fluid pressure remains within safe ranges, thereby reducing, minimizing, and/or eliminating the risk of patient harm or discomfort from pressure of the fluid as it is introduced into the patient.

In some embodiments, the portion 207 of the disposable set can be a portion of a damping device (e.g., the damping device 102 of FIG. 1). For example, a damping device can include one or more diaphragms having one or more cavities configured to reduce pressure pulsations in fluid flowing through the disposable set. Continuing with this example, a diaphragm, a body portion, and/or a cavity of the damping device can correspond to the diaphragm 213, the rim structure 211, and/or the cavity 216 of FIG. 2, respectively. Thus, the pressure sensor 103 can be aligned and brought into contact with the diaphragm of the damping device to determine a pressure of fluid flowing through the cavity of the damping device. Further details regarding damping devices can be found in International (PCT) Application No. PCT/US2021/027428, which is incorporated by reference herein in its entirety.

Figure 4:
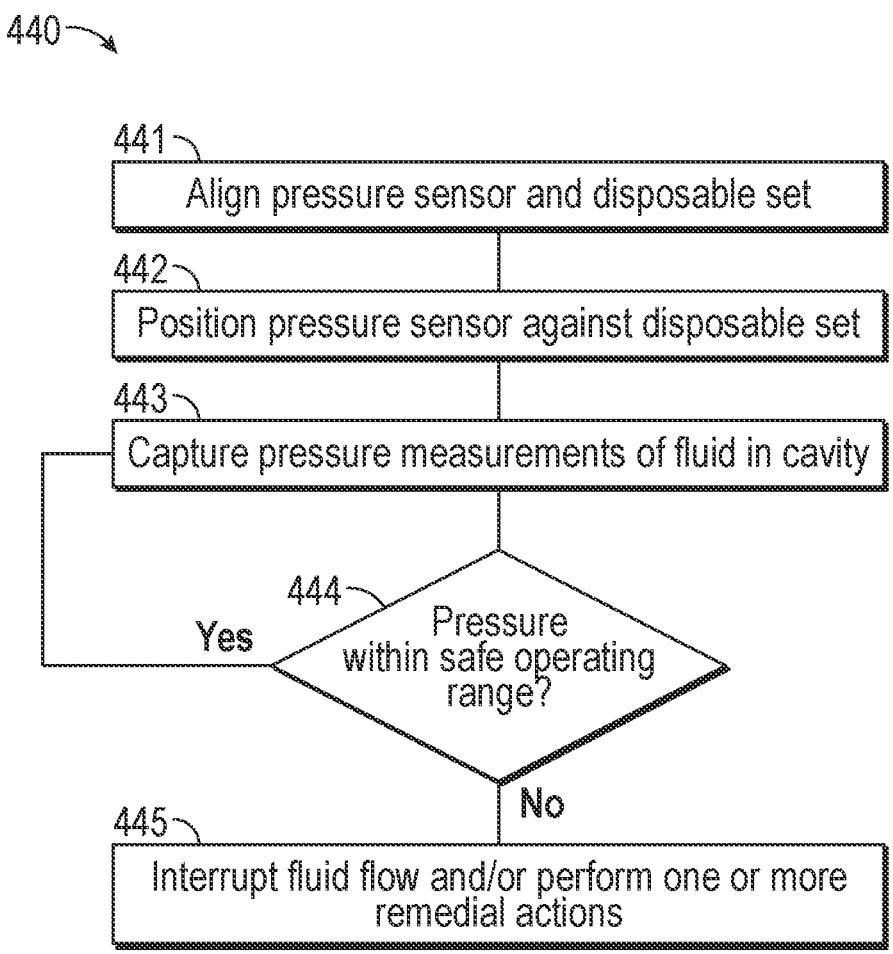
FIG. 4 is a flow diagram illustrating a method of measuring pressure of an isolated fluid in accordance with various embodiments of the present technology.

FIG. 4 is a flow diagram illustrating a method 440 for measuring pressure of an isolated fluid in accordance with various embodiments of the present technology. For example, the method 440 can be a method of measuring pressure of a fluid (e.g., a dialysate or another solution) flowing through a portion (e.g., the portion 207 of FIG. 2) of a disposable set (e.g., the disposable set 107 of FIG. 1) of an APD system (e.g., the system 100 of FIG. 1). The method 440 is illustrated as a set of blocks, steps, operations, or processes 441-445. All or a subset of the blocks 441-445 can be executed at least in part by various components of a system, such as the APD system 100 of FIG. 1. For example, all or a subset of the blocks 441-445 can be executed at least in part by a pump, a pressure sensor, a damping device, fluid lines, and/or other portions of a disposable set. Additionally, or alternatively, all or a subset of the blocks 441-445 can be executed at least in part by an operator (e.g., a user, a patient, a caregiver, a family member, a physician, etc.) of the system. Furthermore, any one or more of the blocks 441-445 can be executed in accordance with the discussion above. Many of the blocks 441-445 of the method 440 are discussed in detail below with reference to FIGS. 2 and 5A-5C for the sake of clarity and understanding.

The method 440 begins at block 441 by aligning a pressure sensor with a disposable set. In some embodiments, aligning the pressure sensor with the disposable set can include aligning the pressure sensor with a portion of the disposable set, such as with a diaphragm similar to the diaphragm discussed above with respect to FIGS. 2-3D. For example, FIG. 2 illustrates the pressure sensor 203 aligned with the diaphragm 213 of the portion 207 of the disposable set such that the diaphragm 213, the indenter 224, the load cell 222, and the linear actuator 226 are positioned or aligned along a common axis. A mount or clamp (e.g., on an APD machine) can be employed to stably and removably position the portion of the disposable set in a fixed orientation as part of the alignment process. For example, an operator can position the portion 207 of the disposable set into a mount such that an outer surface 213a of the diaphragm 213 is positioned generally beneath and/or is generally facing the indenter 224 of the pressure sensor 203. Before and/or while positioning the portion 207 of the disposable set in the mount, the pressure sensor 203 (e.g., the indenter 224 of the presser sensor 203) can be placed in a retracted position (e.g., as shown in FIG. 2) such that the diaphragm 213 is flat, is undeformed, and/or does not contact the pressure sensor 203. Continuing with this example, after the portion 207 of the disposable set is placed in the fixed orientation, the pressure sensor 203 can be positioned such that the pressure sensor 203 is aligned with the portion 207 of the disposable set. All or a subset of the block 441 of the method 440 can be performed without a fluid actively flowing through the disposable set and/or before a fluid enters the cavity 216 of the portion 207 of the disposable set.

At block 442, the method 440 continues by positioning the pressure sensor against the disposable set. In some embodiments, positioning the pressure sensor against the disposable set includes moving the pressure sensor such that the pressure sensor contacts and/or deforms the diaphragm of the disposable set. For example, referring to FIG. 5A, the linear actuator 226 can advance the indenter 224 and/or the load cell 222 to place the indenter 224 in contact with the diaphragm 213. The linear actuator 226, the load cell 222, and the indenter 224 can be considered a rigid element because its deflection under a load is small in comparison to other elements of the system, such as the diaphragm 213. Thus, continuing to advance the indenter 224 beyond initial contact with the diaphragm 213 can increase an amount of deformation exhibited by the diaphragm 213 with little (e.g., small, minimal, inconsequential, etc.) to no deflection of the pressure sensor 203.

Deformation of the diaphragm 213 via contact with the indenter 224 results in a certain applied force that is measured by the load cell 222 of the pressure sensor 203. In particular, the load cell 222 outputs an electrical signal in response to the applied force. The electrical signal can be processed (e.g., by a microcontroller or other processor of the system) and calibrated for the particular load cell 222 or for the particular type of load cell such that subsequent electrical signals output by the load cell 222 directly correspond to a magnitude of a force applied to the load cell 222.

When the cavity 216 is empty of fluid or another pressure source (other than ambient air pressure) acting on the diaphragm 213 from within the cavity 216, the applied force measured by the load cell 222 is referred to hereinafter as a "preload force," is due to a restoring force of the diaphragm 213 alone as the diaphragm 213 is deformed, and is represented by arrow 552 in FIG. 5A. In some embodiments, positioning the pressure sensor against the disposable set can include advancing the indenter 224 of the pressure sensor 203 against the outer surface 213a of the diaphragm 213 until the load cell measures a preload force of a desired magnitude. Stated another way, the linear actuator 226 can advance the indenter 224 and/or the load cell 222 against the diaphragm 213 until an electrical signal output from the load cell 222 reaches a threshold level. In some embodiments, the corresponding preload force can be recorded as a "zero-offset force" and can be used for later calculations of pressure of fluid within the cavity 216, as described in greater detail below.

The choice of a threshold level for the preload/zero-offset force can be most easily shown by example. Consider, for example, a system in which the intended pressure measurement range is −8 kPa to +10 kPa, the indenter 224 of the pressure sensor 203 will contact most of the outer surface 213a of the diaphragm 213, the contact area is 4 cm$^2$, and the force applied by fluid pressure within the cavity 216 ranges from −3.2 N to +4 N. Because the diaphragm 213 would separate from the indenter 224 under negative forces applied against the indenter 224, a minimum measured force can be set at 1 N to provide a safety margin and reduce the possibility of the force dropping below 0 N. The zero-offset force can therefore be set at a minimum of 4.2 N such that the force measured by the load cell 222 varies from 1 N to 8.2 N over the full range of applied fluid pressures. The load cell 222 selected for the pressure sensor 203 can be configured to measure a range of forces that exceeds the expected range of forces measured by the load cell 222 over the full range of applied fluid pressures. Continuing with the above example, a load cell 222 configured to measure a 10 N or 15 N range of forces that includes the entire expected range of forces (i.e., 1 N to 8.2 N in the above example) measured by the load cell 222 can be selected for the pressure sensor 203.

In some embodiments, excess zero-offset force can be avoided for two reasons. First, increasing the zero-offset force can require a load cell 222 capable of measuring a larger range of forces, and load cells 222 configured to measure larger ranges of forces tend to have lower resolution and be less accurate. Second, increasing the zero-offset force can result in greater deformation of the diaphragm 213. An increase in the amount of deformation of the diaphragm can result in inelastic, non-recoverable deformation of the diaphragm material. For example, a diaphragm 213 formed of a polymer may be subject to relaxation (short term) or creep (long term), especially at elevated temperatures, as the amount of deformation of the diaphragm 213 increases. Inelastic deformation can negatively affect the accuracy of pressure measurements captured by the pressure sensor 203.

In some embodiments, loss of accuracy due to inelastic deformation of the diaphragm 213 can be minimized via choice of diaphragm material. Additionally, or alternatively, in embodiments in which usage of the pressure sensor 203 and a diaphragm 213 includes one or more periods during which the fluid pressure is known to be zero, the preload force can be reset at the zero-offset force to compensate for any inelastic deformation. For example, if the preload force is found to have dropped below a threshold value, the linear actuator 226 can slightly advance the indenter 224 against the diaphragm 213 to (a) reduce internal stresses and relaxation in the material of the diaphragm 213 and (b) increase the preload force back to a zero-offset force of an acceptable value.

In alternative embodiments, the pressure sensor 203 (e.g., the load cell 222 and/or the indenter 224) can remain in a fixed position. In these embodiments, rather than the pressure sensor 203 moving towards the diaphragm, the portion 207 of the disposable set including the diaphragm 213 can be moved toward and/or positioned against the pressure sensor 203 (e.g., against the indenter 224) (a) such that the pressure sensor 203 contacts and/or deforms the diaphragm 213 and/or (b) until an electrical signal output from the load cell 222 in response to a preload force applied to the load cell 222 reaches a threshold level. In these and other embodiments, the portion 207 of the disposable set can be moved toward and/or positioned against the pressure sensor 203 using a mount or clamp (e.g., on an APD machine) that holds the portion 207 of the disposable set. Such a mount or clamp can be used in lieu of a linear actuator and/or electric motor in the pressure sensor 203 in some embodiments.

Referring back to FIG. 4, at block 443, the method 440 continues by capturing one or more pressure measurements of fluid in the cavity 216. In some embodiments, capturing a pressure measurement of fluid includes determining a force applied against the indenter of the pressure sensor through the diaphragm 213 of the portion 207 of the disposable set as a result of pressure of fluid within the cavity 216 of the portion 207. For example, FIG. 5B illustrates the effects of fluid in the cavity 216 under positive pressure. A force applied by the fluid against the indenter 224 of the pressure sensor 203 through the diaphragm 213 and generally on axis with the load cell 222 is illustrated as arrow 556 in FIG. 5B. The force measured by the load cell 222 of the pressure sensor 203 is the sum of the zero-offset force and the force applied by the fluid against the indenter 224 due to positive fluid pressure. As shown, the force (arrow 556) applied by the fluid against the indenter 224 as a result of the positive pressure of the fluid operates in the same direction (e.g., toward the load cell 222) as the pre-load/zero-offset force (arrow 552). Thus, the load cell 222 can output an electrical signal that corresponds to a force that is greater than the zero-offset force.

As another example. FIG. 5C illustrates the effects of fluid in the cavity 216 under negative pressure. A force acting on the indenter 224 through the diaphragm 213 and generally on axis with the load cell 222 is illustrated as arrow 557 in FIG. 5C. The force measured by the load cell 222 of the pressure sensor 203 is the sum of the zero-offset force and the force acting on the indenter 224 due to negative fluid pressure. As shown, the force (arrow 557) acting on the indenter 224 as a result of the negative pressure of the fluid operates in an opposite direction (e.g., away from the load cell 222) as the pre-load/zero-offset force (arrow 552). Thus, the load cell 222 can output an electrical signal that corresponds to a force that is lesser than the zero-offset force.

The force acting on the indenter 224 through the diaphragm 213 due to fluid pressures within the cavity 216 and that is measured by the load cell 222 depends on a geometry of the diaphragm 213 and a geometry of the indenter 224. The measured force is at least as great as the pressure of the fluid times the contact area of the indenter 224 against the diaphragm 213 and is no more than the pressure of the fluid times the total surface area of the diaphragm 213. Thus, as discussed above with respect to FIG. 2, shaping the indenter 224 such that an outer contacting surface 225 of the indenter is convexly curved (viewed from beneath the indenter 224, such as at a location between the indenter 224 and the outer surface 213*a* of the diaphragm 213 in FIG. 2) can facilitate positioning the indenter 224 against the outer surface 213*a* of the diaphragm 213 and deforming the diaphragm 213 (*a*) such that the outer surface 225 of the indenter 224 matches a natural curvature of the diaphragm 213 due to pressure alone and/or (b) such that a contact area between the outer surface 225 of the indenter 224 and the diaphragm 213 is nearly equivalent to a surface area (e.g., of the outer surface 213*a* or the inner surface 213*b*) of the diaphragm 213. Such an arrangement between the indenter 224 and the diaphragm 213 can facilitate transmitting nearly all of a force applied against an inner surface 213*b* of the diaphragm 213 to the load cell 222 and can greatly simplify calculation of pressure from force measurements captured by the load cell 222. Stated another way, because the contact area between the shaped indenter 224 and the outer surface 213*a* of the diaphragm 213 is nearly equivalent to the surface area of the diaphragm 213, the calculation of the force exerted on the diaphragm due to positive or negative fluid pressure within the cavity 216 can be simplified to pressure of the fluid times the surface area of the diaphragm 213. Thus, the pressure of the fluid can be directly calculated using Equation 1 below:

$$\text{Pressure} = \frac{(\text{Measured\_Force} - \text{Zero\_Offset\_Force})}{\text{Diaphragm\_Surface\_Area}} \quad \text{Equation 1}$$

Furthermore, because the shaped indenter 224 fully supports the diaphragm 213 and prevents it from moving (e.g., by matching the natural curvature of the diaphragm 213 due to pressure alone), there can be little to no change in an amount of deformation of the diaphragm 213 over the full working range of pressures (e.g., of fluid flowing through a disposable set of an APD system). As such, the pressure sensor 203 can be less sensitive to variations in thickness or modulus of the diaphragm 213 or to stiffness of the joint at the location where the diaphragm 213 and the rim structure 211 are connected. In turn, the pressure sensor 203 can be less sensitive to variations that may exist between a portion 207 of a first disposable set and a portion 207 of a second disposable set, meaning that the pressure sensor 203 can provide consistent measurements of pressure regardless of part-to-part variations in disposable sets used in the system.

On the other hand, if (a) the geometry of the indenter 224 and/or the diaphragm 213 results in the indenter 224 contacting a portion of the diaphragm 213 that is smaller than the surface area of the diaphragm 213 and/or (b) the diaphragm 213 is deformed in a different manner such that it is not fully supported by the indenter 224, then the relationship between force measured by the load cell 222 and the pressure of the fluid within the cavity 216 must be determined by analysis (such as finite element analysis) or experimental results. In addition, the pressure sensor 203 can be more sensitive to variations in thickness or modulus of the diaphragm 213 or to stiffness of the joint at the location where the diaphragm 213 and the rim structure 211 are connected. As such, any analysis or experiments performed to determine the relationship between force measured by the load cell 222 and the pressure of the fluid with the cavity 216 may only be valid for that corresponding diaphragm 213 and/or that corresponding portion 207 of the disposable set. In other words, the calculation of pressure of the fluid within the cavity 216 when a non-convexly curved indenter 224 is used is more complicated than the calculation of pressure of the fluid within the cavity 216 when a convexly-curved indenter 224 is used, and any analysis or experiments performed for a diaphragm 213 of a first disposable set may need to be repeated for a diaphragm 213 of a second (e.g., a next) disposable set when a non-convexly curved indenter 224 is used.

Referring again to FIG. 4, the method 440 continues at block 444 by determining whether a fluid pressure measured by the pressure sensor is within a safe operating range. In some embodiments, the safe operating range can include fluid pressures at which there is little risk of patient harm or discomfort from pressure of the fluid as it is introduced into or is drained out of the patient. For example, a safe operating range can include pressures from about −1.5 kPa to about +1.5 kPa. If the method 440 determines that the fluid pressure measured by the pressure sensor is within the safe operating range, the method 440 can return to block 443 to capture a next pressure measurement of fluid within the cavity 216 of the portion 207 of the disposable set. On the other hand, if the method 440 determines that the fluid pressure measured by the pressure sensor exceeds or is below the safe operating range, the method 440 can proceed to block 445.

At block 445, the method 440 continues by interrupting the flow of fluid through the disposable set and/or taking one or more other remedial actions. In some embodiments, interrupting the flow of fluid can include interrupting a dialysis cycle. In these and other embodiments, the one or more other remedial actions can include bringing the fluid pressure to within the safe operating range (e.g., using a pump or damping device of the system). In these and still other embodiments, the one or more other remedial actions can include generating and/or triggering an alert (e.g., to the user or patient) that pressure of the fluid is outside of the safe operating range.

Although the steps of the method 440 are discussed and illustrated in a particular order, the method 440 illustrated in FIG. 4 is not so limited. In other embodiments, the method 440 can be performed in a different order. In these and other embodiments, any of the steps of the method 440 can be performed before, during, and/or after any of the other steps of the method 440. Moreover, a person of ordinary skill in the relevant art will recognize that the illustrated method 440 can be altered and still remain within these and other embodiments of the present technology. For example, one or more steps of the method 440 illustrated in FIG. 4 can be omitted and/or repeated in some embodiments.

A non-limiting example specific to an APD system will now be provided for the sake of clarity and understanding. For APD, typical dialysate pressure ranges (a) from about 0 kPa to about +10 kPa when introducing dialysate into a patient and (b) from about 0 kPa to about −10 kPa when draining dialysate from the patient. Thus, to measure pressure over this full range and allow a buffer for transient over-pressure, a pressure sensor having an operating range of about −20 kPa to about +20 kPa can be provided. An indenter of the pressure sensor can be placed into contact with a diaphragm of a portion of a disposable set and can be advanced to deform the diaphragm to a desired zero-offset force. In some embodiments, the stiffness of the diaphragm and the amount of deformation can be chosen such that the zero-offset force against a load cell of the pressure sensor is equivalent to a force that would be produced by 25 kPa of pressure when the diaphragm is not deformed.

During therapy, a positive fluid pressure acts on the indenter of the pressure sensor through the diaphragm and increases the force on the load cell of the pressure sensor (e.g., up to a maximum of about +45 kPa). A negative fluid pressure acts on the indenter through the diaphragm and decreases the force on the load cell (e.g., down to a minimum of about 5 kPa). Thus, an approximately equal positive and negative pressure range of fluid pressure can be measured while always maintaining a positive force against the indenter and the load cell of the pressure sensor. As such, the load cell provided for the pressure sensor can be configured to a range forces that corresponds to measuring a range of pressures from about 0 kPa to about 50 kPa when the diaphragm is not deformed.

Figure 6A:
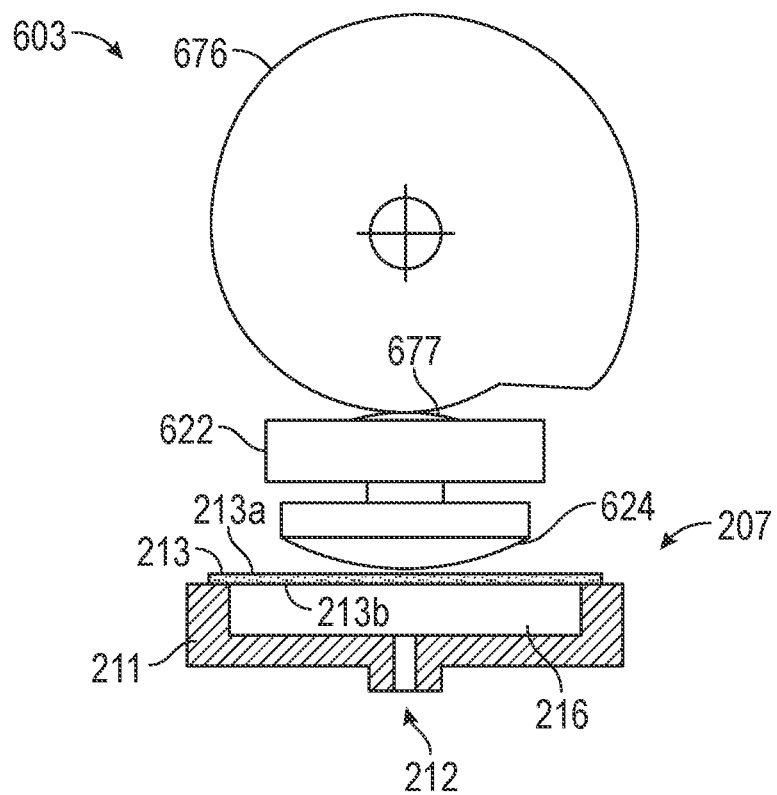
FIGS. 6A and 6B are partially schematic, side views of a pressure sensor and a partially schematic, cross-sectional side view of a portion of a disposable set, each configured in accordance with various embodiments of the present technology.
Figure 6B:
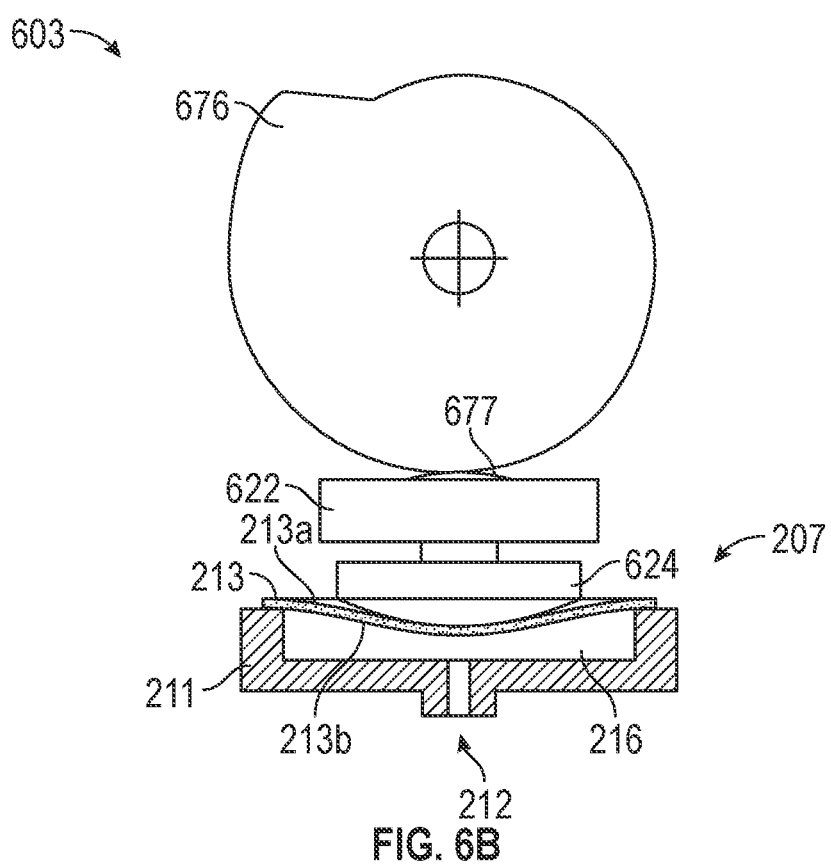

FIGS. 6A and 6B are partially schematic, side views of a pressure sensor 603 configured in accordance with various embodiments of the present technology and aligned with the portion 207 of the disposable set from FIG. 2. The pressure sensor 603 can be the pressure sensor 103 of FIG. 1 or another pressure sensor of the present technology. The pressure sensor 603 is similar to the pressure sensor 203 of FIG. 2 in that the pressure sensor 603 includes a shaped indenter 624 and a load cell 622 positioned between the shaped indenter 624 and an actuator 676. The actuator 676 of the pressure sensor 603, however, is a cam 676 (rather than a linear actuator 226) that rotates against a pad 677 or roller affixed to the load cell 222. Rotation of the cam 676 can occur about a fixed axis, can be achieved via an electric motor through a gear reducer, and/or can be controlled by a microcontroller (not shown). As the cam 676 is rotated, the cam 676 acts against the pad 677, which can translate (e.g., advance or retract) the indenter 224 and/or the load cell 222 generally along an axis that passes through the indenter 224, the load cell 222, and a center of the cam 676. In some embodiments, the load cell 222 and/or the indenter 224 can be moved over their full ranges of motion within one complete rotation of the cam 676. In these and other embodiments, the pressure sensor 603 can include a linear guide (not shown) to constrain movement of the load cell 222 and/or the indenter 224 to the axis that passes through the indenter 224, the load cell 222, and a center of the cam 676. The pressure sensor 603 can otherwise be operated in a manner generally similar to the pressure sensor 203 of FIG. 2.

Figure 7:
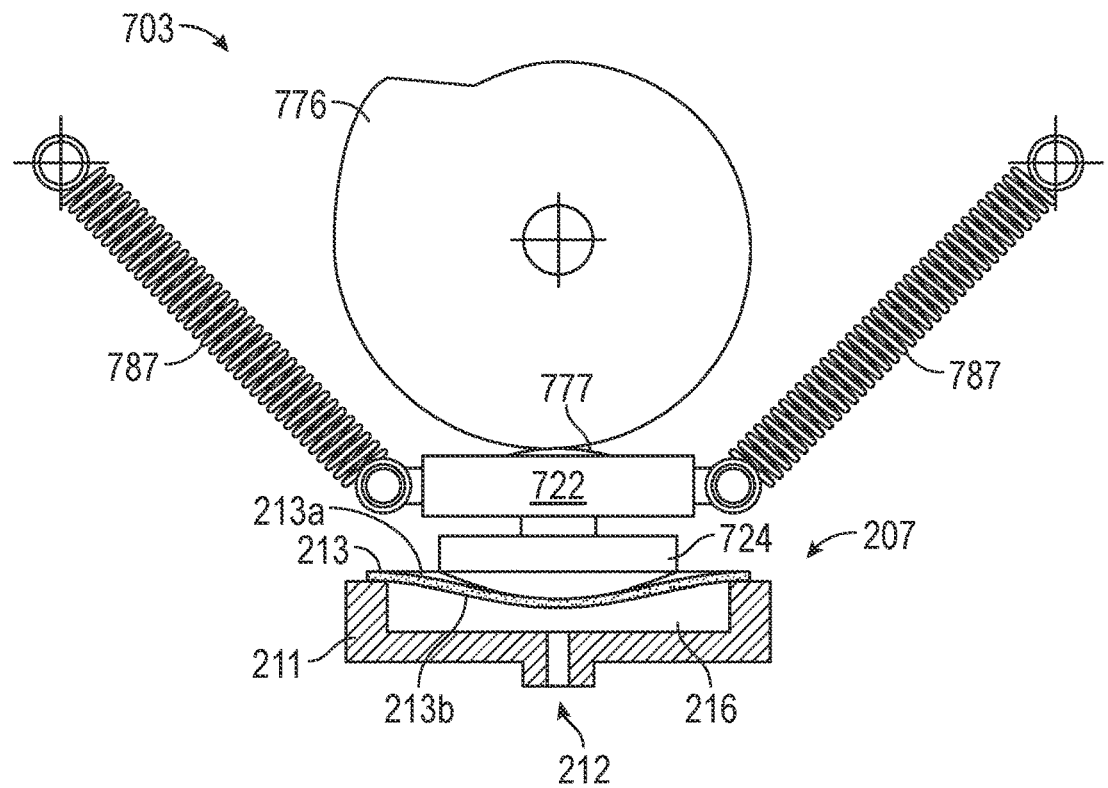
FIG. 7 is a partially schematic, side view of a pressure sensor and a partially schematic, cross-sectional, side view of a portion of a disposable set, each configured in accordance with various embodiments of the present technology.

FIG. 7 is a partially schematic, side view of a pressure sensor 703 configured in accordance with various embodiments of the present technology and aligned with the portion 207 of the disposable set of FIG. 2. The pressure sensor 703 can be the pressure sensor 103 of FIG. 1 or another pressure sensor of the present technology. The pressure sensor 703 is similar to the pressure sensor 603 of FIG. 6A and FIG. 6B in that the pressure sensor 703 includes a shaped indenter 724, a cam 776, a pad 777, and a load cell 722 positioned between the shaped indenter 724 and the cam 776. The pressure sensor 703 differs from the pressure sensor 603, however, in that the pressure sensor 703 further includes one or more springs 787 that hold the load cell 222 and/or the shaped indenter 724 firmly against the cam 776. In embodiments in which a mechanism holding the pressure sensor 703 can be rotated to different orientations, the weight of the indenter 724 can be free to move above the load cell 722, which can affect force measurements captured by the load cell 7222. Thus, the one or more springs 787 can be employed to ensure the weight of the indenter 724 remains below the load cell 722 without changing the action of the indenter 724 against the diaphragm 213. (The one or more springs 787 can be employed in other pressure sensors of the present technology, such as in the pressure sensor 203 of FIG. 2 to eliminate weight and/or backlash errors that occur with a lead screw mechanism and/or another linear drive mechanism or actuator.) The pressure sensor 703 can otherwise be operated in a manner generally similar to the pressure sensor 203 of FIG. 2 and/or the pressure sensor 603 of FIG. 6A and FIG. 6B.

Figure 8:
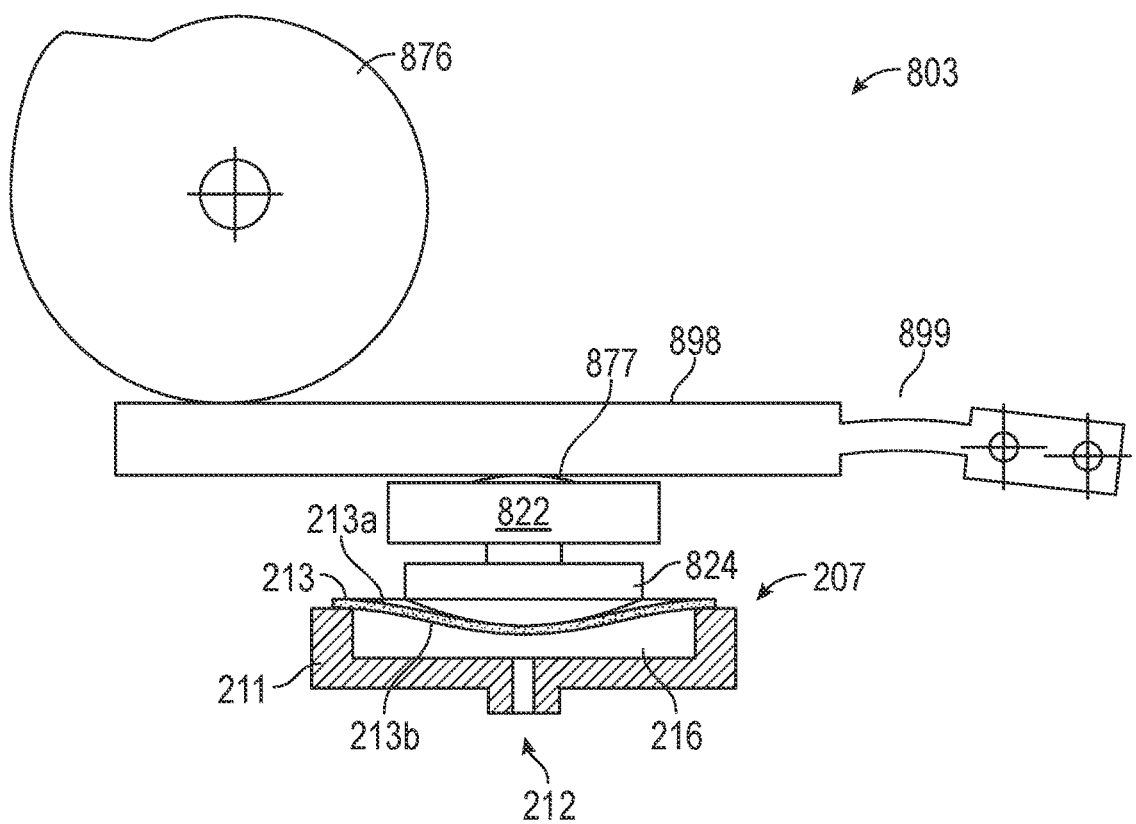
FIG. 8 is a partially schematic, side view of a pressure sensor and a partially schematic, cross-sectional, side view of a portion of a disposable set, each configured in accordance with various embodiments of the present technology.

FIG. 8 is a partially schematic, side view of a pressure sensor 803 configured in accordance with various embodiments of the present technology and aligned with the portion 207 of the disposable set of FIG. 2. The pressure sensor 803 can be the pressure sensor 103 of FIG. 1 or another pressure sensor of the present technology. The pressure sensor 803 is generally similar to the pressure sensor 603 of FIG. 6A and FIG. 6B and the pressure sensor 703 of FIG. 7 in that the pressure sensor 803 includes a shaped indenter 824, a cam 876, a pad 877, and a load cell 822 positioned between the cam 876 and the shaped indenter 824. The pressure sensor 803 differs from the pressure sensors 603 and 703, however, in that the pressure sensor 803 further includes a pivoting arm 898 (e.g., in lieu of a linear guide mechanism), and the cam 876 is laterally offset from the load cell 822 and the shaped indenter 824. The pivoting arm 898 is configured to rotate about a pivot point and includes a hinge section 899. The hinge section 899 can be an elastically bending section of the pivoting arm 898 that (a) provides a high-resolution pivot without static friction and/or (b) acts as a spring to maintain contact with the cam 876, similar to the one or more springs 787 of FIG. 7. Alternatively, a rotating pivot and a separate spring may be employed in the pressure sensor 803 in lieu of the pivoting arm 898 and/or the hinge section 899. In some embodiments, a length of the pivoting arm 898 can be much greater than the required range of motion of the indenter 824. Thus, deviation (if any) from linear motion toward the diaphragm 213 will be very small. In addition, laterally offsetting the cam 876 a greater distance from the pivot point of the pivoting arm 898 than the load cell 822 and the shaped indenter 824 provides increased leverage and mechanical resolution. The pressure sensor 803 can otherwise be operated in a manner generally similar to the pressure sensor 203 of FIG. 2, the pressure sensor 603 of FIG. 6A and FIG. 6B, and/or the pressure sensor 703 of FIG. 7.

C. EXAMPLES

Several aspects of the present technology are set forth in the following examples. Although several aspects of the present technology are set forth in examples specifically directed to systems, devices, and methods; any of these aspects of the present technology can similarly be set forth in examples directed to any of systems, devices, and methods in other embodiments.

1. An automated peritoneal dialysis (APD) system, comprising:
   a disposable set, wherein—
      at least a portion of the disposable set comprises a rim structure having an opening, a diaphragm connected to the rim structure about a periphery of the opening, and a port,
      the diaphragm has an outer surface and an inner surface opposite the outer surface,
      the rim structure and at least a portion of the inner surface of the diaphragm define a cavity, and
      the cavity is in fluid communication with fluid lines of the disposable set via the port; and
   a pressure sensor configured to measure pressure of dialysate flowing through the disposable set, the pressure sensor including a load cell and an indenter operably connected to the load cell, wherein
      the indenter has a convex contacting surface,
      the indenter is movable along an axis such that, when the diaphragm is aligned with the axis, the convex contacting surface of the indenter can be brought into contact with the outer surface of the diaphragm and deform the diaphragm inward toward the cavity, and
      when the convex contacting surface of the indenter contacts the outer surface of the diaphragm, the load cell is configured to measure a force applied to the indenter by the diaphragm and/or by the dialysate within the cavity.

2. The APD system of example 1 wherein, when the convex contacting surface of the indenter contacts the outer surface of the diaphragm and deforms the diaphragm inward toward the cavity, an area of contact between the convex contacting surface of the indenter and the outer surface of the diaphragm is equivalent to a surface area of the inner surface of the diaphragm exposed to the dialysate within the cavity.

3. The APD system of example 1 or example 2 wherein a curvature of the convex contacting surface of the indenter matches a curvature of the diaphragm when the diaphragm is deformed due only to pressure of the dialysate within the cavity.

4. The APD system of any of examples 1-3 wherein the pressure sensor further comprises a linear actuator configured to translate the indenter along the axis.

5. The APD system of example 4 wherein the linear actuator includes a lead screw.

6. The APD system of any of examples 1-3 wherein the pressure sensor further comprises a cam, and wherein rotation of the cam is configured to translate the indenter along the axis.

7. The APD system of example 6 wherein the pressure sensor further comprises a spring configured to hold the load cell and the indenter against the cam.

8. The APD system of example 6 wherein:
the pressure sensor further comprises a pivoting arm positioned between the load cell and the cam;
the cam is positioned at a first location along the pivoting arm that is laterally offset from a second location along the pivoting arm at which the load cell and the indenter are positioned.

9. The APD system of any of examples 1-8 wherein the diaphragm is affixed to the rim structure about the periphery of the opening such that the cavity is hermetically sealed through the opening.

10. The APD system of any of examples 1-9 wherein:
the diaphragm and the rim structure are a single integrated component; and
a first portion of the single integrated component corresponding to the diaphragm is thinner and more flexible than a second portion of the single integrated component corresponding to the rim structure.

11. A method of measuring pressure of fluid flowing through a disposable set of an automated peritoneal dialysis (APD) system, the method comprising:
aligning a pressure sensor of the APD system with a diaphragm of the disposable set;
deforming the diaphragm using an indenter of the pressure sensor such that (a) a curved surface of an indenter of the pressure sensor contacts an outer surface of the diaphragm, and (b) a load cell of the pressure sensor operably connected to the indenter measures a zero-offset force corresponding to a restoring force applied against the indenter by the diaphragm; and measuring, using the pressure sensor, a pressure of a fluid flowing through the disposable set and in contact with an inner surface of the diaphragm opposite the outer surface.

12. The method of example 11 wherein aligning the pressure sensor with the diaphragm includes mounting a portion of the disposable set including the diaphragm in a mount configured to align the portion of the disposable set with the pressure sensor.

13. The method of example 11 or example 12 wherein deforming the diaphragm includes deforming the diaphragm such that a contact area between the curved surface of the indenter and the outer surface of the diaphragm is equivalent to a surface area of the inner surface of the diaphragm exposed to the fluid.

14. The method of any of examples 11-13 wherein deforming the diaphragm includes advancing the indenter against the outer surface of the diaphragm.

15. The method of example 14 wherein the zero-offset force is a predetermined value, and wherein advancing the indenter against the outer surface of the diaphragm includes advancing the indenter against the outer surface of the diaphragm until the load cell measures the zero-offset force.

16. The method of example 14 or example 15 wherein:
the zero-offset force is a predetermined value; and
advancing the indenter includes:
   monitoring, using a microcontroller, force measurements captured by the load cell; and
   automatically advancing the indenter using a linear actuator and an electric motor until the load cell measures the zero-offset force.

17. The method of any of examples 11-16, further comprising comparing the pressure of the fluid to a safe operating pressure range.

18. The method of example 17, further comprising interrupting fluid flow through the disposable set when the pressure of the fluid is outside of the safe operating pressure range.

19. The method of any of examples 11-18, further comprising increasing the zero-offset force by further deforming the diaphragm using the indenter of the pressure sensor to account for inelastic deformation of the diaphragm.

20. An automated peritoneal dialysis system, comprising:
a diaphragm positioned over an opening in a disposable set that includes one or more fluid lines, the diaphragm affixed to the disposable set about a periphery of the opening; and
a pressure sensor configured to measure a pressure of fluid flowing through the disposable set, the pressure sensor having a load cell and an indenter,
   wherein the indenter is linearly moveable along an axis such that, when the diaphragm is aligned with the axis, a convexly curved surface of the indenter can be brought into contact with an outer surface of the diaphragm, and
   wherein, when the convexly curved surface of the indenter is in contact with the outer surface of the diaphragm, the load cell is configured to measure a force applied to the load cell by the diaphragm and/or by the fluid flowing through the disposable set.

C. CONCLUSION

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. Moreover, the terms "connect" and "couple" are used interchangeably herein and refer to both direct and indirect connections or couplings. For example, where the context permits, element A "connected" or "coupled" to element B can refer (i) to A directly "connected" or directly "coupled" to B and/or (ii) to A indirectly "connected" or indirectly "coupled" to B.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and for various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. An automated peritoneal dialysis (APD) system, the system comprising:
 a disposable set, wherein at least a portion of the disposable set includes
  a rim structure having an opening,
  a diaphragm connected to the rim structure about a periphery of the opening, and
  a port,
  the diaphragm having an outer surface and an inner surface opposite the outer surface, the rim structure and at least a portion of the inner surface of the diaphragm defining a cavity, and
  the cavity is in fluid communication with fluid lines of the disposable set via the port; and
 a pressure sensor configured to measure pressure of dialysate flowing through the disposable set, the pressure sensor including a load cell and an indenter operably connected to the load cell, wherein
  the indenter has a convex contacting surface, the indenter is movable along an axis such that, when the diaphragm is aligned with the axis, the convex contacting surface of the indenter can be brought into contact with the outer surface of the diaphragm and deform the diaphragm inward toward the cavity, and
  when the convex contacting surface of the indenter contacts the outer surface of the diaphragm, the load cell is configured to measure a force applied to the indenter by the diaphragm and/or by the dialysate within the cavity.

2. The APD system of claim 1, wherein, when the convex contacting surface of the indenter contacts the outer surface of the diaphragm and deforms the diaphragm inward toward the cavity, an area of contact between the convex contacting surface of the indenter and the outer surface of the diaphragm is equivalent to a surface area of the inner surface of the diaphragm exposed to the dialysate within the cavity.

3. The APD system of claim 1, wherein a curvature of the convex contacting surface of the indenter matches a curvature of the diaphragm when the diaphragm is deformed due only to pressure of the dialysate within the cavity.

4. The APD system of claim 1, wherein the pressure sensor further comprises a linear actuator configured to translate the indenter along the axis.

5. The APD system of claim 4, wherein the linear actuator includes a lead screw.

6. The APD system of claim 1, wherein the pressure sensor further comprises a cam, and wherein rotation of the cam is configured to translate the indenter along the axis.

7. The APD system of claim 6, wherein the pressure sensor further comprises a spring configured to hold the load cell and the indenter against the cam.

8. The APD system of claim 6, wherein:
 the pressure sensor further comprises a pivoting arm positioned between the load cell and the cam, the cam is positioned at a first location along the pivoting arm that is laterally offset from a second location along the pivoting arm at which the load cell and the indenter are positioned.

9. The APD system of claim 1, wherein the diaphragm is affixed to the rim structure about the periphery of the opening such that the cavity is hermetically sealed through the opening.

10. The APD system of claim 1 wherein:
 the diaphragm and the rim structure are a single integrated component, and a first portion of the single integrated component corresponding to the diaphragm is thinner and more flexible than a second portion of the single integrated component corresponding to the rim structure.

11. A method of measuring pressure of fluid flowing through a disposable set of an automated peritoneal dialysis (APD) system, the method comprising:
 aligning a pressure sensor of the APD system with a diaphragm of the disposable set;
 deforming the diaphragm using an indenter of the pressure sensor such that
  (a) a curved surface of an indenter of the pressure sensor contacts an outer surface of the diaphragm, and
  (b) a load cell of the pressure sensor operably connected to the indenter measures a zero-offset force corresponding to a restoring force applied against the indenter by the diaphragm; and
 measuring, using the pressure sensor, a pressure of a fluid flowing through the disposable set and in contact with an inner surface of the diaphragm opposite the outer surface.

12. The method of claim 11, wherein aligning the pressure sensor with the diaphragm includes mounting a portion of the disposable set including the diaphragm in a mount configured to align the portion of the disposable set with the pressure sensor.

13. The method of claim 11, wherein deforming the diaphragm includes deforming the diaphragm such that a contact area between the curved surface of the indenter and the outer surface of the diaphragm is equivalent to a surface area of the inner surface of the diaphragm exposed to the fluid.

14. The method of claim 11, wherein deforming the diaphragm includes advancing the indenter against the outer surface of the diaphragm.

15. The method of claim 14, wherein the zero-offset force is a predetermined value, and wherein advancing the indenter against the outer surface of the diaphragm includes advancing the indenter against the outer surface of the diaphragm until the load cell measures the zero-offset force.

16. The method of claim 14, wherein:
 the zero-offset force is a predetermined value; and
 advancing the indenter includes:
 monitoring, using a microcontroller, force measurements captured by the load cell; and
 automatically advancing the indenter using a linear actuator and an electric motor until the load cell measures the zero-offset force.

17. The method of claim 11, further comprising comparing the pressure of the fluid to a safe operating pressure range.

18. The method of claim 17, further comprising interrupting fluid flow through the disposable set when the pressure of the fluid is outside of the safe operating pressure range.

19. The method of claim 11, further comprising increasing the zero-offset force by further deforming the diaphragm using the indenter of the pressure sensor to account for inelastic deformation of the diaphragm.

20. An automated peritoneal dialysis system, comprising:
a diaphragm positioned over an opening in a disposable set that includes one or more fluid lines, the diaphragm affixed to the disposable set about a periphery of the opening; and
a pressure sensor configured to measure a pressure of fluid flowing through the disposable set, the pressure sensor having a load cell and an indenter,
wherein the indenter is linearly moveable along an axis such that, when the diaphragm is aligned with the axis, a convexly curved surface of the indenter can be brought into contact with an outer surface of the diaphragm, and
wherein, when the convexly curved surface of the indenter is in contact with the outer surface of the diaphragm, the load cell is configured to measure a force applied to the load cell by the diaphragm and/or by the fluid flowing through the disposable set.

\* \* \* \* \*